(12) United States Patent
Dunlop (10) Patent No.: US 12,038,110 B2
(45) Date of Patent: Jul. 16, 2024

(54) APPARATUS FOR PATIENT WARMING

(71) Applicant: Colin Dunlop, East Ryde (AU)

(72) Inventor: Colin Dunlop, East Ryde (AU)

( * ) Notice: Subject to any disclaimer, the term of this patent is extended or adjusted under 35 U.S.C. 154(b) by 494 days.

(21) Appl. No.: 17/283,680

(22) PCT Filed: Sep. 26, 2019

(86) PCT No.: PCT/AU2019/000120
§ 371 (c)(1),
(2) Date: Apr. 8, 2021

(87) PCT Pub. No.: WO2020/061614
PCT Pub. Date: Apr. 2, 2020

(65) Prior Publication Data
US 2021/0337764 A1 Nov. 4, 2021

(30) Foreign Application Priority Data

Sep. 30, 2018 (AU) .................................. 2018101469

(51) Int. Cl.
*F16L 23/036* (2006.01)
*A61D 99/00* (2006.01)
(Continued)

(52) U.S. Cl.
CPC ............ *F16L 23/036* (2013.01); *A61D 99/00* (2013.01); *F16L 5/027* (2013.01); *F16L 23/22* (2013.01); *F16L 37/113* (2013.01); *F16L 37/26* (2013.01)

(58) Field of Classification Search
CPC . F16L 23/22; F16L 37/113; F16L 5/08; F16L 23/036; F16L 5/027; F16L 37/26; F16B 5/0056; F16B 5/0036; F16B 5/0032
See application file for complete search history.

(56) References Cited

U.S. PATENT DOCUMENTS 2,160,354 A * 5/1939 Evans .................... F16L 37/248
285/73
3,731,956 A * 5/1973 Hanley ................. E04B 1/6116
403/380
(Continued)

FOREIGN PATENT DOCUMENTS

CN 207394191 U 5/2018
DE 3330221 A1 * 3/1985
(Continued)

OTHER PUBLICATIONS

International Search Report dated Nov. 22, 2019 for corresponding International Application No. PCT/AU2019/000120.

*Primary Examiner* — Zachary T Dragicevich
*Assistant Examiner* — James A Linford
(74) *Attorney, Agent, or Firm* — TAROLLI, SUNDHEIM, COVELL & TUMMINO L.L.P.

(57) ABSTRACT

An apparatus for facilitating delivery of conditioned air across a barrier in a cage for holding an animal patient to a blanket arrangement providing the conditioned air to the patient. The apparatus comprising a first duct part, a second duct part and a mounting mechanism arranged to mount the first duct part on one side of the barrier and the second duct part on the other side of the barrier opposite thereto, to provide a duct for ducting conditioned air across the barrier. The barrier comprising bars or mesh, and the apparatus further comprising a seal arrangement to provide at least a partial seal across the bars or mesh. The mounting mechanism comprises a fastening mechanism for fastening the first and second duct parts to each other across the barrier, wherein the fastening mechanism is a keyhole-style fastening arrangement utilising a plurality of headed projections on a flange of the first duct part engagable with respective keyhole-style apertures on a flange of the second duct part.

5 Claims, 10 Drawing Sheets

(51) Int. Cl.
*F16L 5/02* (2006.01)
*F16L 23/22* (2006.01)
*F16L 37/113* (2006.01)
*F16L 37/26* (2006.01)

(56) References Cited

U.S. PATENT DOCUMENTS

| | | | | |
|---|---|---|---|---|
| 4,271,865 A | * | 6/1981 | Galloway | F16L 37/36 251/89.5 |
| 4,587,788 A | * | 5/1986 | Bielicki | E04B 1/6137 403/353 |
| 5,620,314 A | * | 4/1997 | Worton | F04B 9/14 92/162 P |
| 5,632,769 A | | 5/1997 | Kappel | |
| 6,131,958 A | * | 10/2000 | Craig | F16L 37/248 285/136.1 |
| 6,506,960 B1 | * | 1/2003 | Young | A61F 13/53752 604/377 |
| 9,308,122 B2 | | 4/2016 | Dunlop | |
| 2008/0288034 A1 | | 11/2008 | Pierre | |

FOREIGN PATENT DOCUMENTS

| | | | | |
|---|---|---|---|---|
| WO | WO-9302313 A1 | * | 2/1993 | F16L 21/08 |
| WO | 2004052250 A1 | | 12/2003 | |
| WO | WO-2010111750 A1 | * | 10/2010 | A47C 21/04 |

* cited by examiner

APPARATUS FOR PATIENT WARMING

RELATED APPLICATIONS

The present application is a U.S. National Stage application under 35 USC 371 of PCT Application Serial No. PCT/AU2019/000120, filed on 26 Sep. 2019; which claims priority from AU Patent Application No. 2018101469, filed 30 Sep. 2018, the entirety of both of which are incorporated herein by reference.

TECHNICAL FIELD

This invention relates to an apparatus for keeping a patient warm. In particular the present invention is described with reference for keeping a veterinary patient warm during care. More particularly the invention is described with reference to an apparatus for delivering conditioned air across a barrier and a blanket arrangement for providing conditioned air to the patient, particularly, but not exclusively, for use in veterinary care.

BACKGROUND

There are many circumstances in human and animal medicine where it is necessary to keep a patient warm to, for example, prevent or treat hypothermia. Forced warm air heating systems have been designed to keep patients warm during surgery and during critical care (e.g. recovery post-surgery).

Blankets have been designed to provide warm air heating for animals during surgery and recovery, see the applicant's earlier International Patent Publication No. WO/2004/052250.

Forced warm air heating systems usually comprise a blanket-type arrangement which comprises at least two layers forming a hollow space between them when air is delivered to the space. The blanket or a portion of the blanket may include one or more air holes, or it may be of a porous/permeable material, to allow warmed air through the blanket to warm the patient. For small animals, blankets having a portion of permeable/porous material are preferred so that the warm air is diffused over the surface of the material.

Forced warm air heating systems also include a heating unit for providing the warmed air, and a conduit, which may be in the form of a hose and/or pipe for delivering the warmed air from the heating unit to the blanket arrangement.

Animal patients during critical care or recovery (e.g. post anaesthesia) are usually caged for their restraint and safety (semi-conscious animals move about and can become injured through misadventures such as falling off treatment tables). Where an animal needs to be warmed during care, in the cage, this leads to a problem in using warmed air heating systems. The heater (with an electricity supply and heating unit, etc) must be placed outside the cage and any blanket arrangement must obviously be placed in the cage. There is therefore difficulty in providing the warm air conduit from the heater to the patient through the cage. The cage door must be properly shut so that the animal can't fall out. This problem is exacerbated by the fact that there are many different types of cages provided for veterinary patients, which, for example, have different diameters of bars, different grill patterns or grill widths for the cage and cage doors. These problems prevent hoses/piping providing heating conduits from being able to pass through a cage door into a cage.

Presently available warm air blanket arrangements typically have only one port by which warm air can enter the blanket (via the conduit). Generally, it is not convenient for the blanket to be moved once the patient is in the cage. Having only one port, say at the head of the blanket, may make it difficult for the warm air to be provided to the blanket without moving it. Having the port at the head end of the blanket (which is usually the case) in many cases, does not provide a convenient position for introducing the warmed air conduit to the port when the blanket arrangement is positioned within a cage.

Cages for animals in veterinary establishments are usually of a form having a solid bottom, ceiling and sides (which may be of metal or wood) and then one or two barred doors on the front of the cage, which swing fully open. As discussed above, trying to pass warmed air from a forced warmed air heating system via a conduit into the cage is difficult. The only option may be the cage door, which presents the further difficulty that the cage door must be able to be opened, sometimes quickly for urgent access.

The applicant's U.S. Pat. No. 9,308,122 discloses an apparatus to deliver conditioned (preferably warm) air through a cage (barrier) by providing a mounting mechanism (or cage door adaptor) having a first duct part to be mounted on one side of the cage thereto, and a second duct part mounted on the opposite side of the cage. The first duct part and second duct part each comprise a plastic sleeve (tubular male member) and an integrally formed flange portion one end of the sleeve. In use the flange portions face each other on opposite sides of the cage (barrier) and mount a flexible membrane sealing arrangement (a ring of open cell foam) disposed there between. A fastening mechanism in the form of nuts and bolts, are used to interconnect the flange portions. The heads of the bolts are placed inside the cage for two reasons, firstly so that the nuts (typically wing nuts) are accessible from outside the cage, and secondly to minimise risk of injury to the animal by protruding objects. In use air conduits are push fitted onto the sleeves of first duct part and second duct part so that conditioned air generated from outside the cage can be delivered to a blanket inside the cage.

Veterinary hospitals typically have many cages used for post operative care of dogs and cats. In the use of the apparatus disclosed in U.S. Pat. No. 9,308,122, many such hospitals do not fit a "adaptor" to each cage door, and instead veterinary staff tend to move the few they have from cage to cage as required. A disadvantage of this is the time required to undo the nuts from the bolts, and another disadvantage is the possibility of misplacing or losing the nut during movement of the mounting mechanism.

The present invention is to provide an apparatus and system that overcomes at least one of the problems associated with the prior art.

SUMMARY OF INVENTION

In a first aspect the present invention consists of an apparatus for facilitating delivery of conditioned air across a barrier in a cage for holding an animal patient to a blanket arrangement providing the conditioned air to said patient, said apparatus comprising a first duct part, a second duct part and a mounting mechanism, said mounting mechanism arranged to mount said first duct part on one side of said barrier and said second duct part on the other side of said barrier opposite said first duct part, to provide a duct for ducting conditioned air across said barrier irrespective of the arrangement of said barrier, said barrier comprising bars or mesh, and the apparatus further comprising a seal arrangement to provide at least a partial seal across the bars or mesh, and said mounting mechanism comprises a fastening mechanism for fastening said first and second duct parts to each other across the barrier, wherein said fastening mechanism is a keyhole-style fastening arrangement utilising a plurality of headed projections on a flange of said first duct part engagable with respective keyhole-style apertures on a flange of said second duct part.

Preferably upon insertion of said headed projections into said respective keyhole-style apertures, the flange of said first duct part is slidably moved relative to the flange of said first second duct part.

Preferably each said keyhole-style aperture has a portion of larger dimension than a curved elongate slot which extends there from, and when said headed projections are inserted into said keyhole-style aperture they are inserted through said portion of larger dimension, and when the flange of said first duct is slidably moved relative to the flange of said first second part, the relative movement is as a result of a twist action.

Preferably each said keyhole aperture has a rib disposed at or near the periphery of the closed end of said elongate slot.

Preferably said seal arrangement comprises of at least one layer of foam disposed on the flange of said first duct part, said layer of foam arranged to make a seal across said barrier when said first and second duct parts are on opposite sides of said barrier.

Preferably said layer of foam arranged to make said seal, is a closed cell foam, which during engagement of said headed projections with said respective keyhole-style apertures of said second duct part, said closed cell foam is compressed, and when said first duct part and second duct part are secured, said closed cell foam returns towards its pre-compressed state whilst remaining between said first and second duct parts.

Preferably in alternative embodiment each said keyhole-style aperture has a portion of larger dimension than a straight elongate slot which extends there from, and when said headed projections are inserted into said keyhole-style aperture they are inserted through said portion of larger dimension, and when the flange of said first duct is slidably moved relative to the flange of said first second part, the relative movement is of a linear action.

In a second aspect the present invention consists in an apparatus for facilitating delivery of conditioned air across a barrier in a cage for holding an animal patient to a blanket arrangement providing the conditioned air to said patient, said barrier comprising bars or mesh, said apparatus comprising a first duct part having a first flange engagable to a second duct part having a second flange, with said barrier and a seal of closed cell foam disposed between said first flange and said second flange, said first flange having a plurality of headed projections engagable with a plurality of respective keyhole-style apertures on said second flange of said second duct part, wherein each said keyhole-style aperture has a portion of larger dimension than a curved elongate slot which extends there from, and when said headed projections are inserted into respective said keyhole-style apertures they are inserted through said portion of larger dimension, and when said first flange of said first duct part is slidably moved relative to said second flange of said second duct part, the relative movement is as a result of a twist action.

Preferably during engagement of said headed projections with said respective keyhole-style apertures of said second duct part, said seal of closed cell foam is compressed, and when said first duct part and second duct part are secured, said closed cell foam returns towards its pre-compressed state whilst remaining between said first and second duct parts and in engagement with said barrier.

In a third aspect the present invention consists in an apparatus for facilitating delivery of conditioned air across a barrier in a cage for holding an animal patient to a blanket arrangement providing the conditioned air to said patient, said barrier comprising bars or mesh, said apparatus comprising:
  a first duct part having a first flange including a plurality of headed projections;
  a second duct part having a second flange including a plurality of keyhole-style apertures, each said keyhole-style aperture has a portion of larger dimension than a curved elongate slot which extends there from;
  a toroidal sealing member of closed cell foam having holes therein mounted to said first flange via said plurality of headed projections; and
  wherein in use said first duct part and said seal is positioned from the inside of said barrier with said headed projections passing through said barrier and said toroidal sealing member abutting against said barrier, and with said second duct part on said opposite side of said cage each said headed projection is inserted into a respective said keyhole-style aperture via said portion of larger dimension, and when said first flange of said first duct is slidably moved relative to said second flange of said first second part, the relative movement is as a result of a twist action, and each said headed projections is aligned with a respective said curved elongate slot of a said keyhole-style aperture, and during the engagement of said headed projections with said respective keyhole-style apertures of said second duct part, said toroidal sealing member is compressed, and when said first duct part and second duct part are secured, said closed cell foam returns towards its pre-compressed state whilst remaining between said first and second duct parts and in engagement with said barrier.

BEST MODE OF CARRYING OUT THE INVENTION

For the purposes of this specification a "keyhole-style aperture" is an aperture having at least two portions, the first portion larger in size than the second portion that extends there from. For example, the keyhole-style aperture may have a first portion with a circular or rectangular, having a diameter or width that is substantially greater than the second portion, say a slot, which extends there from.

For the purposes of this specification a "keyhole-style fastening arrangement" is an arrangement utilising a keyhole-style aperture engagable with a headed projection.

FIGS. 1 to 5 depicts a first embodiment of a ducting apparatus 1, for facilitating delivery of warmed air from a heating (blower) unit 9 across a barrier 3 to a blanket 2. Barrier 3 in this embodiment is a cage door, of a cage for housing an animal patient (not shown). Apparatus 1 which may also be referred to as an "adaptor" is for attachment to barrier 3.

Apparatus (or adaptor) 1 comprises a first duct part 11 and a second duct part 12 (in this example first duct part 11 is inside of the cage door and second duct part 12 is intended for outside the cage door). In this embodiment first duct part 11 and second duct part 12 have sleeve portions 13, 14 respectively which define ports 23, 24 of each duct. Each sleeve portion 13, 14 which is preferably made of plastic, has a flange 15, 16 disposed at one end thereof and integrally formed therewith.

A mounting mechanism, in this embodiment comprises a keyhole-style fastening arrangement that fastens first duct part 11 and second duct part 12 to each other against the bars of cage door 3. The keyhole-style fastening arrangement which fastens first duct part 11 and second m duct part 12 comprises three headed projections 25 on flange 15 of first duct part 11 engagable with three respective keyhole-style apertures 26 on flange 16 of second duct part 12.

In this embodiment each keyhole-style aperture 26 has the shape of a circle 26a at one end with an elongate curved slot 26b extending there from. The circle 26a of keyhole-style aperture 26 is of a size to allow head 27 of projection 25 to pass there through. The diameter of shaft 28 of projection 25 upon which head 27 is mounted, is slightly smaller in diameter than the width of elongate curved slot 26b, so that it can be slid there along.

Apparatus 1 also comprises a sealing arrangement in the form of a toroidal sealing member 30 disposed on the side of flange 15 from which headed projections 25 project. Preferably sealing member 30 is a layer of closed cell foam secured to flange 15 by adhesive. Holes 31 are provided in sealing member 30 so that projections 25 pass through them when sealing member is mounted to flange 15.

In use, when first duct part 11 and second duct part 12 are to be mounted to cage 3, a user (not shown) brings first duct part 11 towards and against cage door 3, such that headed projections 25 pass through cage 3 and sealing member 30 on flange 15 is abutted and held against the inside of cage 3, such that sealing member 30 compresses around the bars of cage door 3 and portions thereof protrude through cage door 3. With headed projections 25 passed through cage door 3, the user brings second duct part 12 towards them and circle portion 26a of each keyhole-style aperture 26 is passed over respective heads 27 of projections 25. Once, circle portions 26a have cleared respective heads 27 and are aligned with respective shafts 28, second duct part 12 is twisted relative to first duct part 11, thereby having shafts 28 slide within respective curved slots 26b. When heads 27 are aligned with slot 26b, they cannot be withdrawn from keyhole-style aperture 26, as the head 27 is larger than the slot. During the bringing together and twisting of second duct part 12 relative to first duct part 11, sealing member 30 is compressed somewhat. However, once second duct part 12 and first duct part 11 are secured and let go of by the user, the closed cell foam of sealing member 30 will return somewhat towards its pre-compressed state, but as it is "sandwiched" between flanges 15, 16 of respective duct parts 11, 12 sealing member 30 provides an effective seal across the bars of cage door 3 (the barrier).

Each keyhole-style aperture 26 has a rib 29 partially encircling the end of its respective curved slot 26b. This rib 29 acts both as stiffener in the vicinity of slot 26b, but also as an engagement seat for head 27 when projection 25 has been inserted through keyhole-style aperture 26, m twisted to slide along slot 26b and locked in place.

In a first arrangement ports 23, 24 provide connectors for connecting the connecting a first conduit part inside the cage (not shown) and a second conduit part 7 outside the cage.

Second conduit part 7 includes a socket connector 60 arranged to mate with the socket connector formed by the sleeve portion 14 of second duct part 12. The rest of first conduit part 7 is a flexible hose 61.

Inside cage 3, a first conduit part (similar to second conduit part 7 but omitted from the figures) is formed from a further socket connector (not shown), arrange to mate with the socket connector formed by sleeve portion 13 of first duct part 11, The rest of first conduit part is formed by a flexible hose, in similar fashion to second conduit part. In a first arrangement the free end of the flexible hose of first conduit part can be inserted into an air entry port of a blanket.

The diameter of first conduit part and second conduit part 7 varies only a little via the ducting apparatus 1, so as to minimise resistance to air flow.

It should be noted that sleeve portion 13 of first duct part 11, has a toroidal lip (or rim) 19 thereon.

Figure 1:
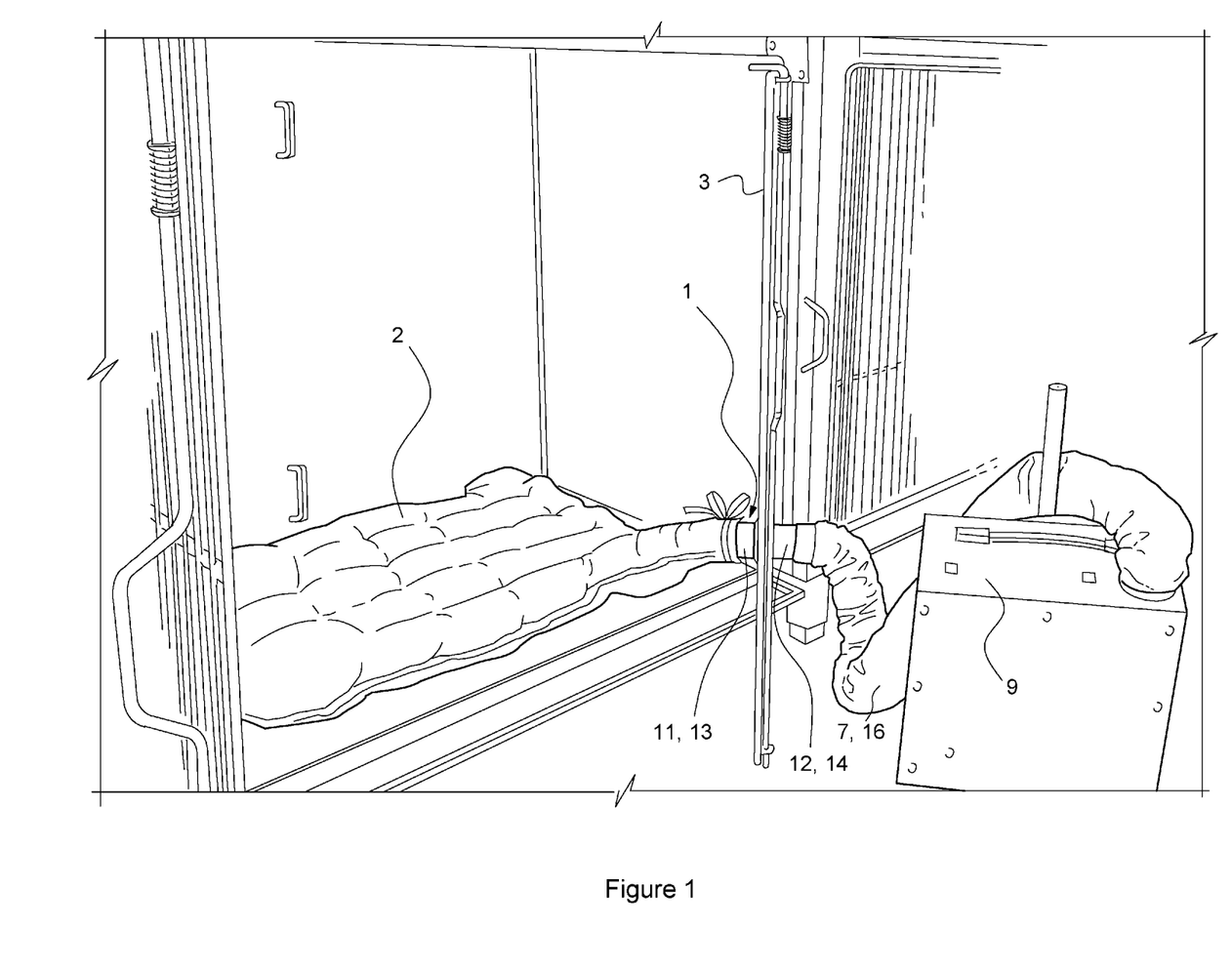
FIG. 1 is a picture of a warmed air heating system for an animal patient, utilising an apparatus in a first embodiment of the invention.
Figure 2:
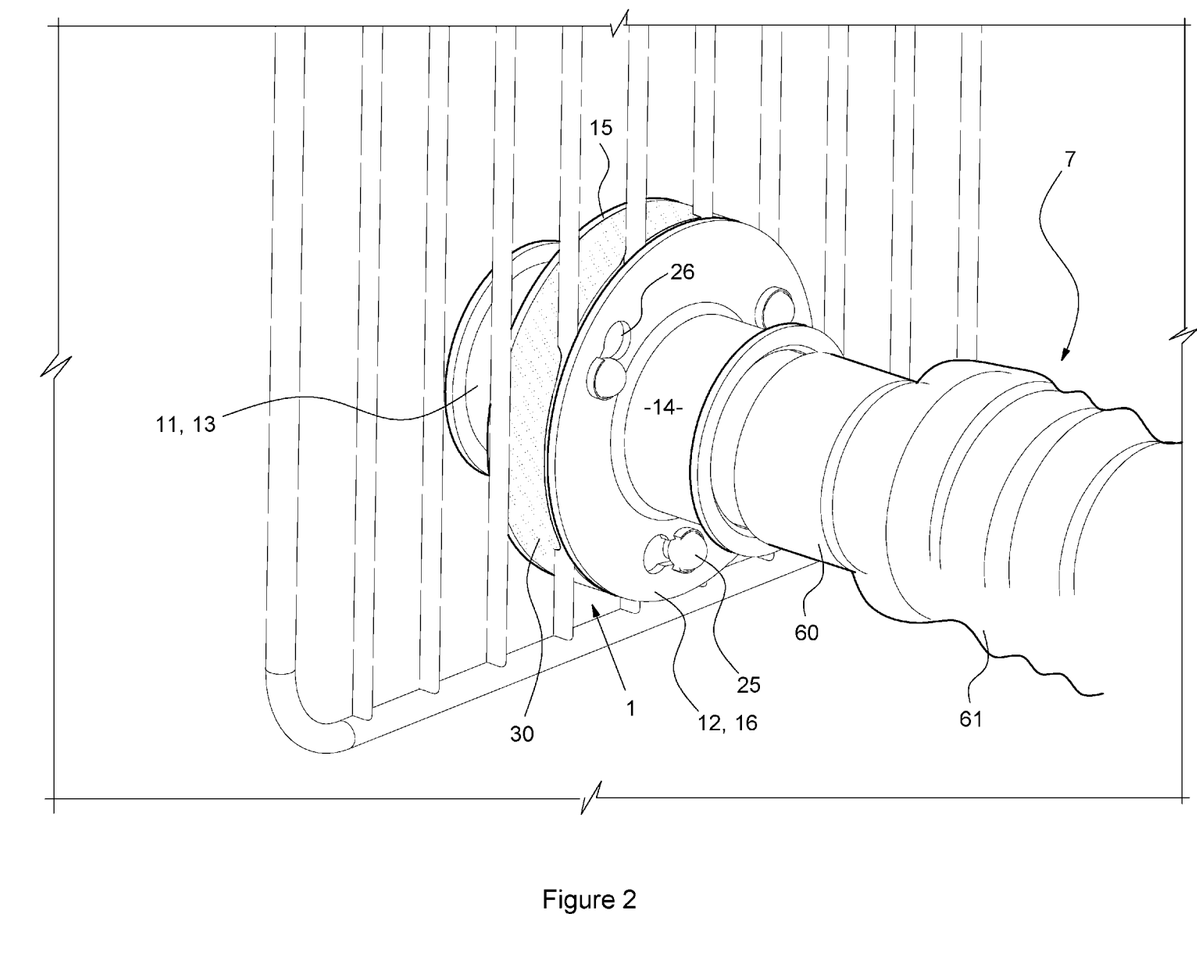
FIG. 2 is an enlarged perspective view of the apparatus of FIG. 1 attached to a cage door (viewed from outside the cage door).
Figure 3:
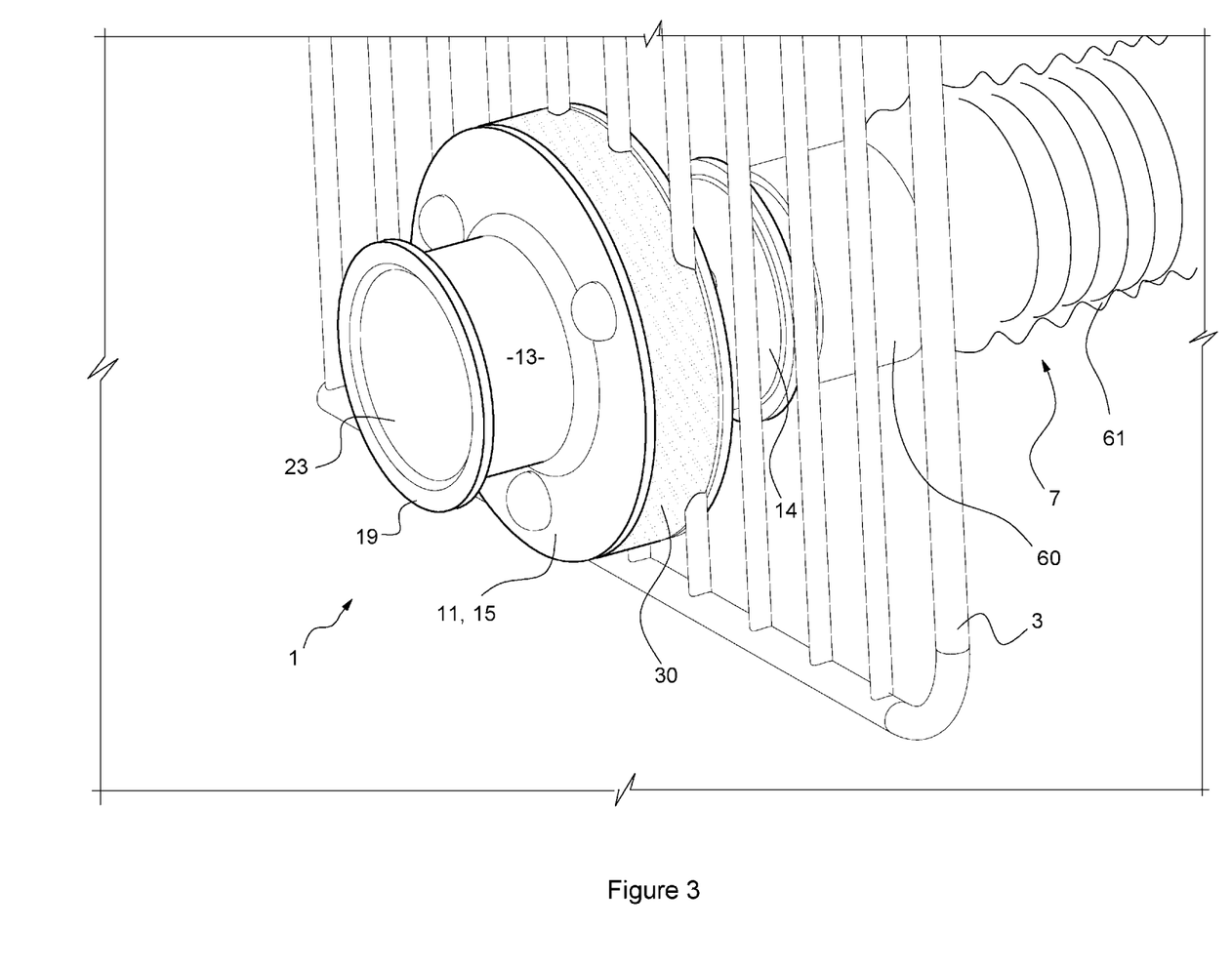
FIG. 3 is an enlarged perspective view of the apparatus of FIG. 1 attached to a cage door (viewed from inside the cage door).
Figure 4:
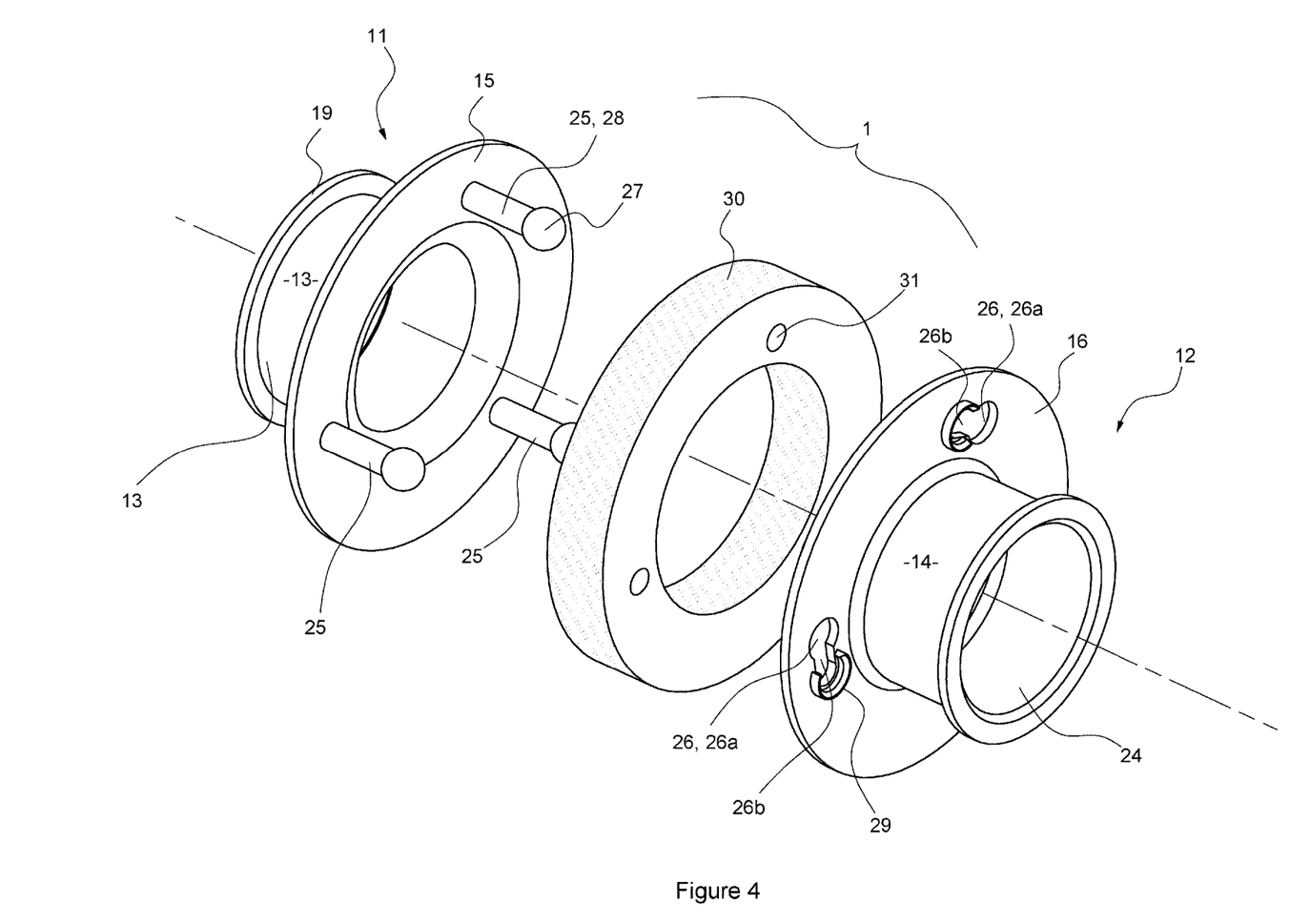
FIG. 4 is an exploded perspective view of the apparatus shown in FIG. 1.
Figure 5:
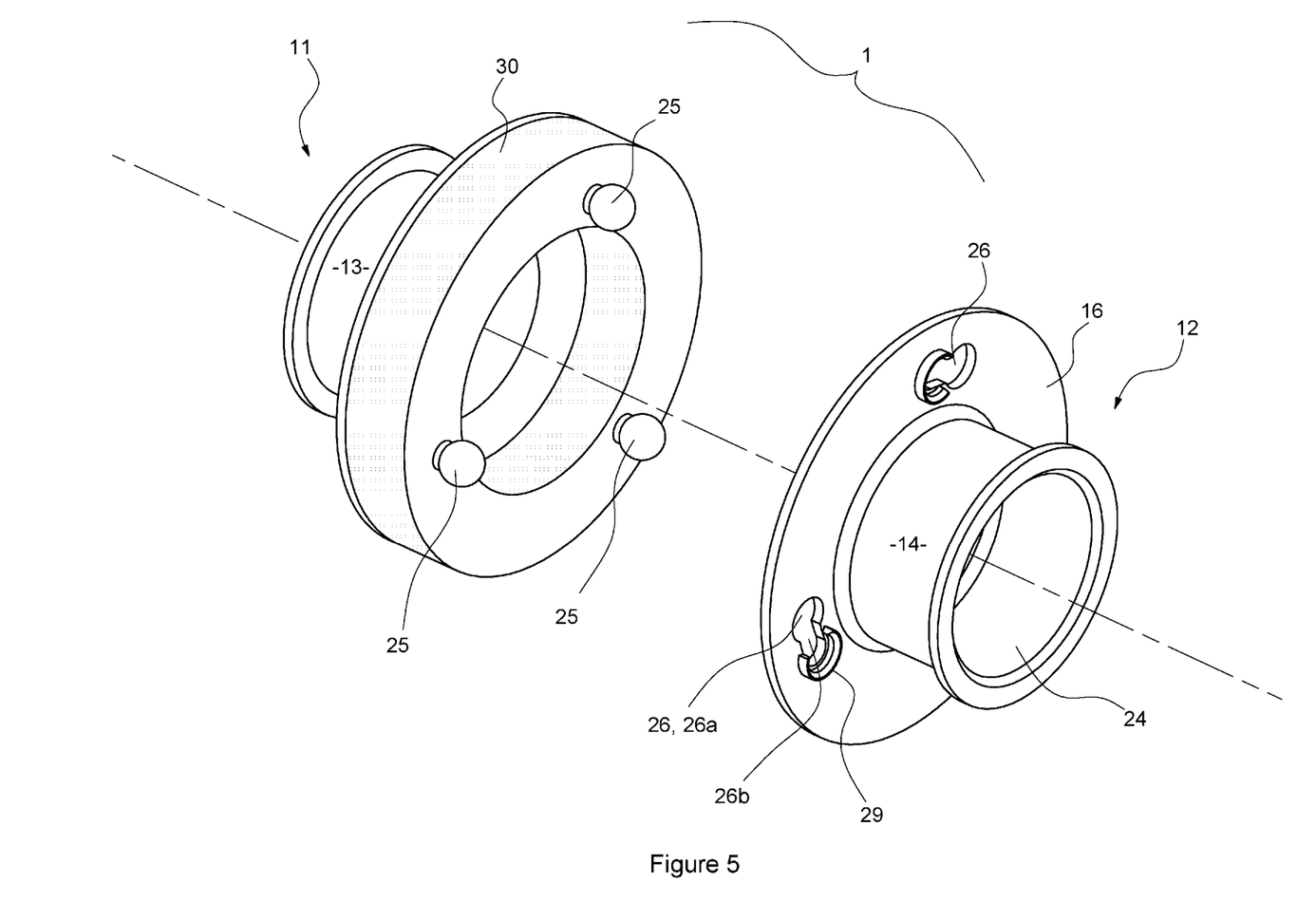
FIG. 5 is an exploded perspective view of the apparatus shown in FIG. 1 with sealing member attached to the first duct part.

In a second arrangement, rather than use the not shown first conduit part to interconnect a blanket 2 (inside the cage) to first conduit part 11, blanket 2 could be provided with a substantially elongate air entry port 8 that could be fitted over sleeve portion 13 and toroidal lip 19. Elongated air entry port 8 would be tied (or clamped) to sleeve portion 13 between flange 15 and toroidal lip 19. FIG. 1 depicts such second arrangement where elongate air entry port 8 of blanket 2 is tied directly sleeve portion 13 of first conduit part 11.

Figure 6:
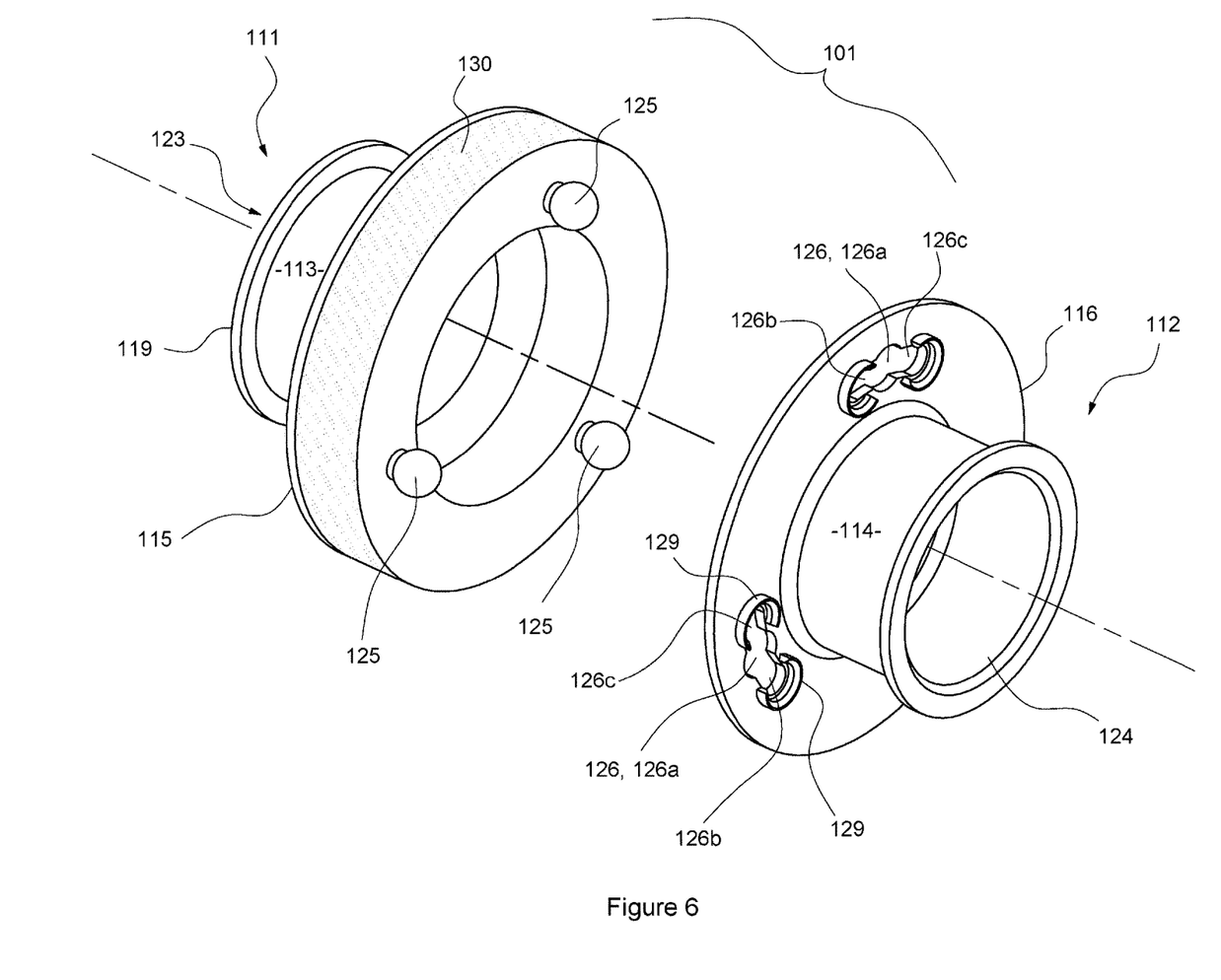
FIG. 6 is a perspective view of an apparatus according to a second embodiment where the first duct part and second duct part are disconnected from one another.
Figure 7:
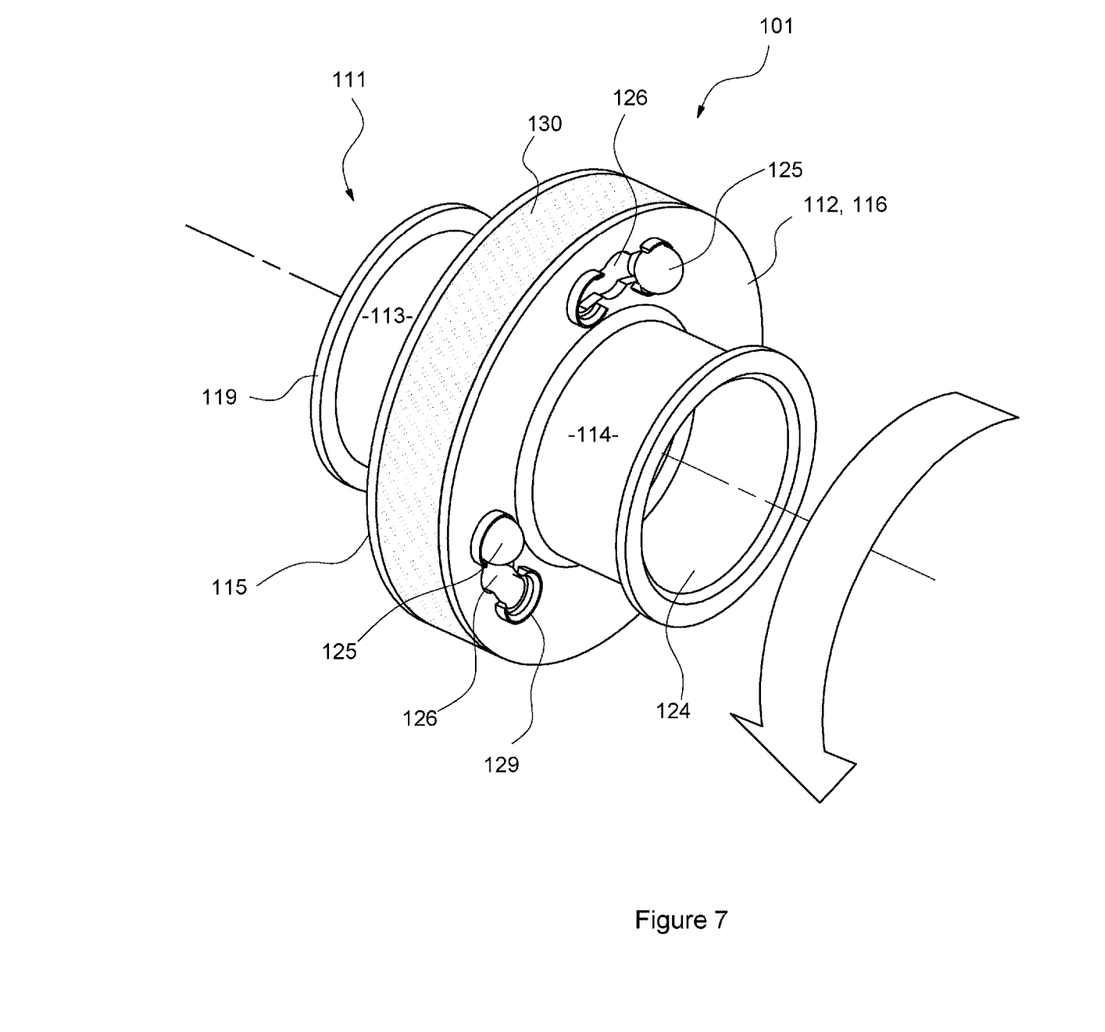
FIG. 7 is a perspective view of the apparatus of FIG. 6 where the first duct part and second duct part are connected to each other.

FIGS. 6 and 7, depict a second embodiment of an apparatus device 101, similar to apparatus 1, in which it comprises a first duct part 111 and a second duct part 112, each having respective sleeve portions 113, 114 respectively which define ports 123, 124 of each duct. Each sleeve portion 113, 114 has a flange 115,116 disposed at one end thereof and integrally formed therewith.

Flange 115 has three projections 125, similar to those of projections 25 of the first embodiment, and a sealing member 130 mounted thereto.

The primary difference in this second embodiment is that flange 116 of the second duct part 112 has a different type of keyhole-style aperture 126 with a centrally disposed circle 126a and two elongate curved slots 126b, 126c each extending from opposite sides of circle 126a.

The circle 126a of keyhole-style aperture 126 is of a size to allow the head of projection 125 to pass there through. However, the user (not shown) once having inserted projections 125 has the option of turning first duct part 111 relative to second duct part 112 in either direction as it is possible to slide along either of elongate curved slots 126b, 126c. In effect this apparatus 1, gives the user the flexibility of choosing which way to turn and connect, but the keyhole-style aperture 126 and projections 125 engage with each other in exactly the same way for engagement purposes, as in the first embodiment. Likewise the sealing member 130 functions in the same manner as sealing member 30 of the first embodiment.

Each keyhole-style aperture 126 has ribs 129 partially encircling the end of its respective curved slots 126b, 126c. This rib 129 has a similar function to rib 29 of the first embodiment.

Likewise, toroidal lip 119 has a similar function to lip 19 of the first embodiment.

Figure 8:
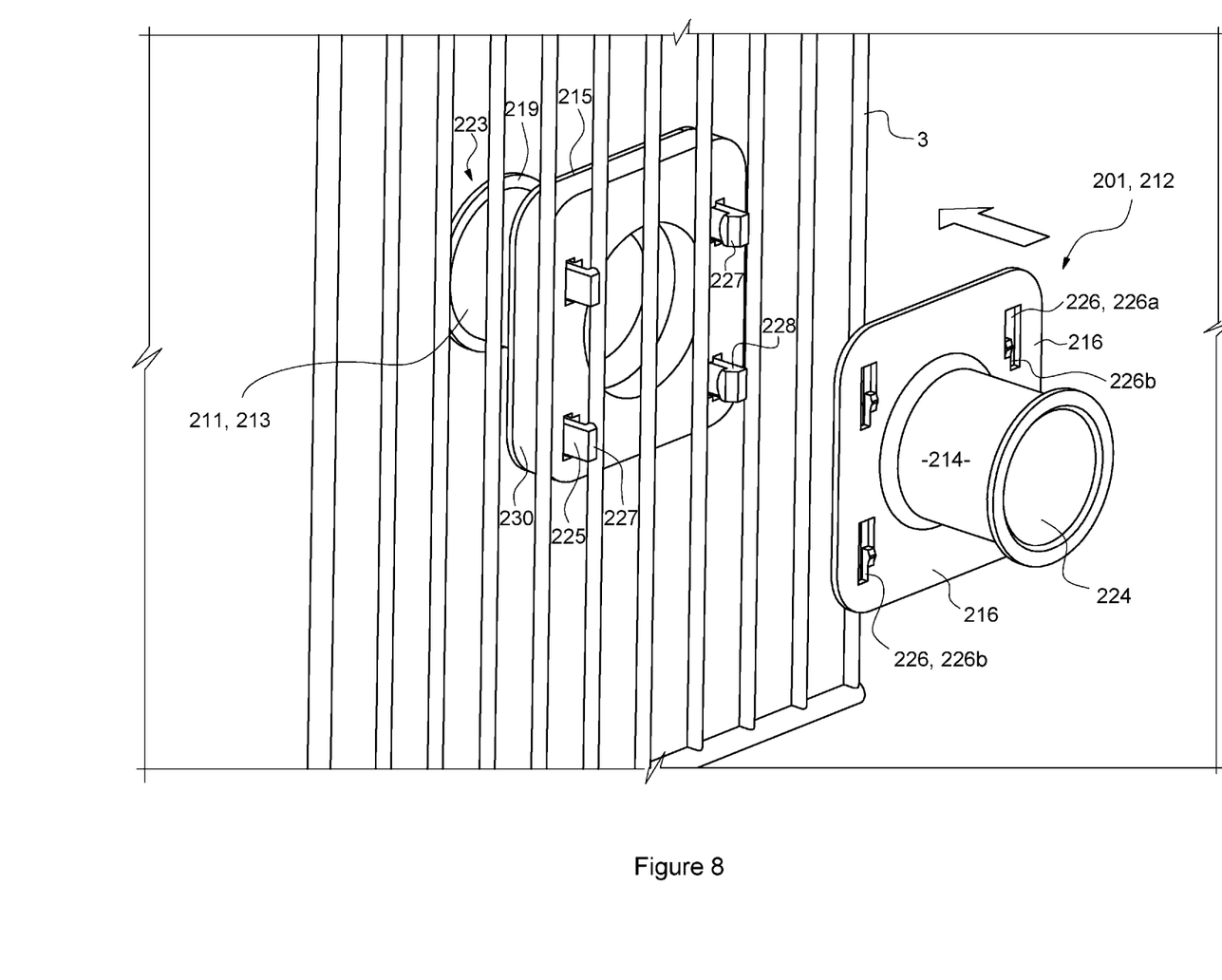
FIG. 8 is a perspective view of the apparatus according to a third embodiment with its first duct part (and sealing member) on an opposed side of a cage door to that of the second duct part.
Figure 9:
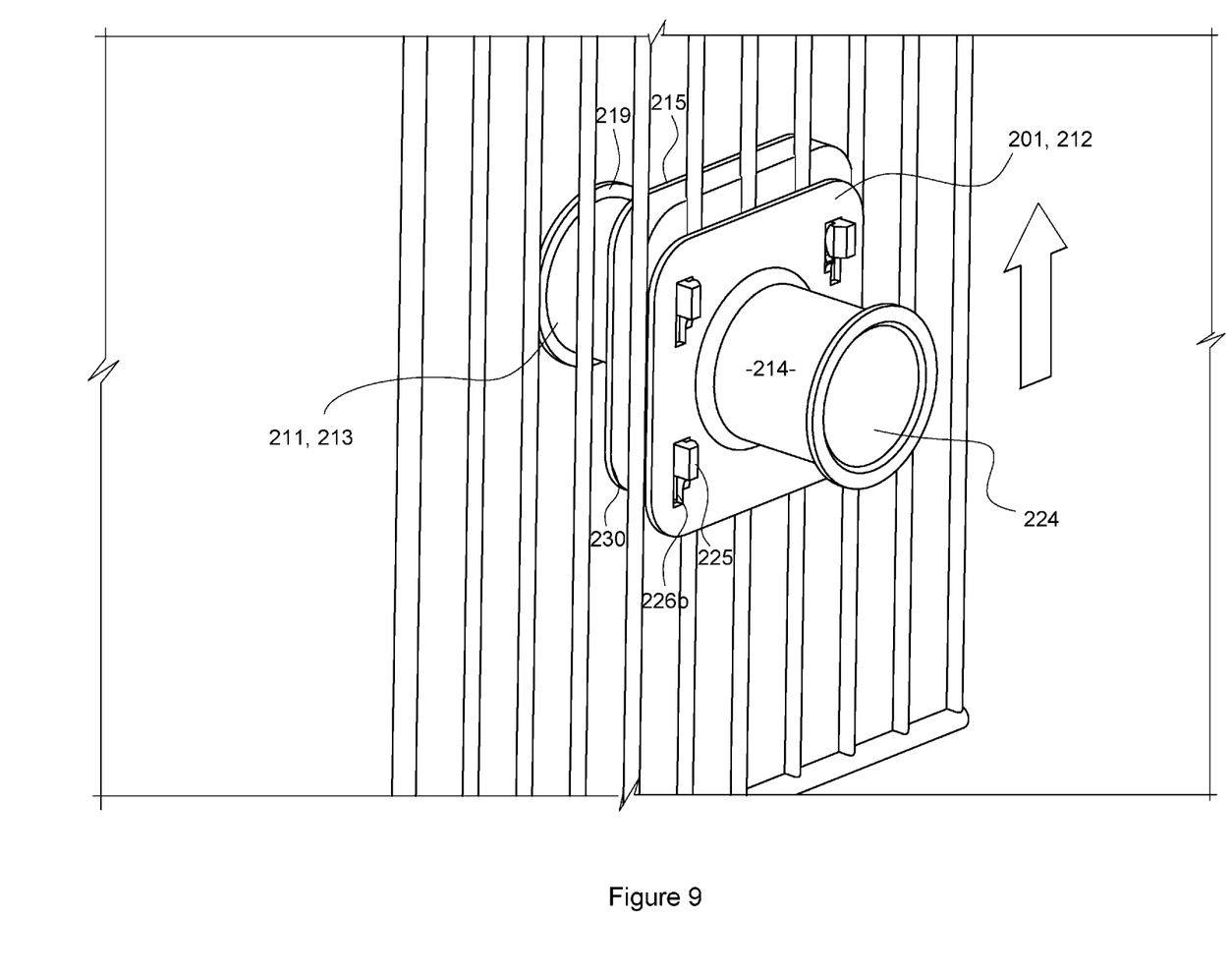
FIG. 9 is a perspective view of the apparatus shown in FIG. 8 with the second duct part brought into engagement with the first duct part.
Figure 10:
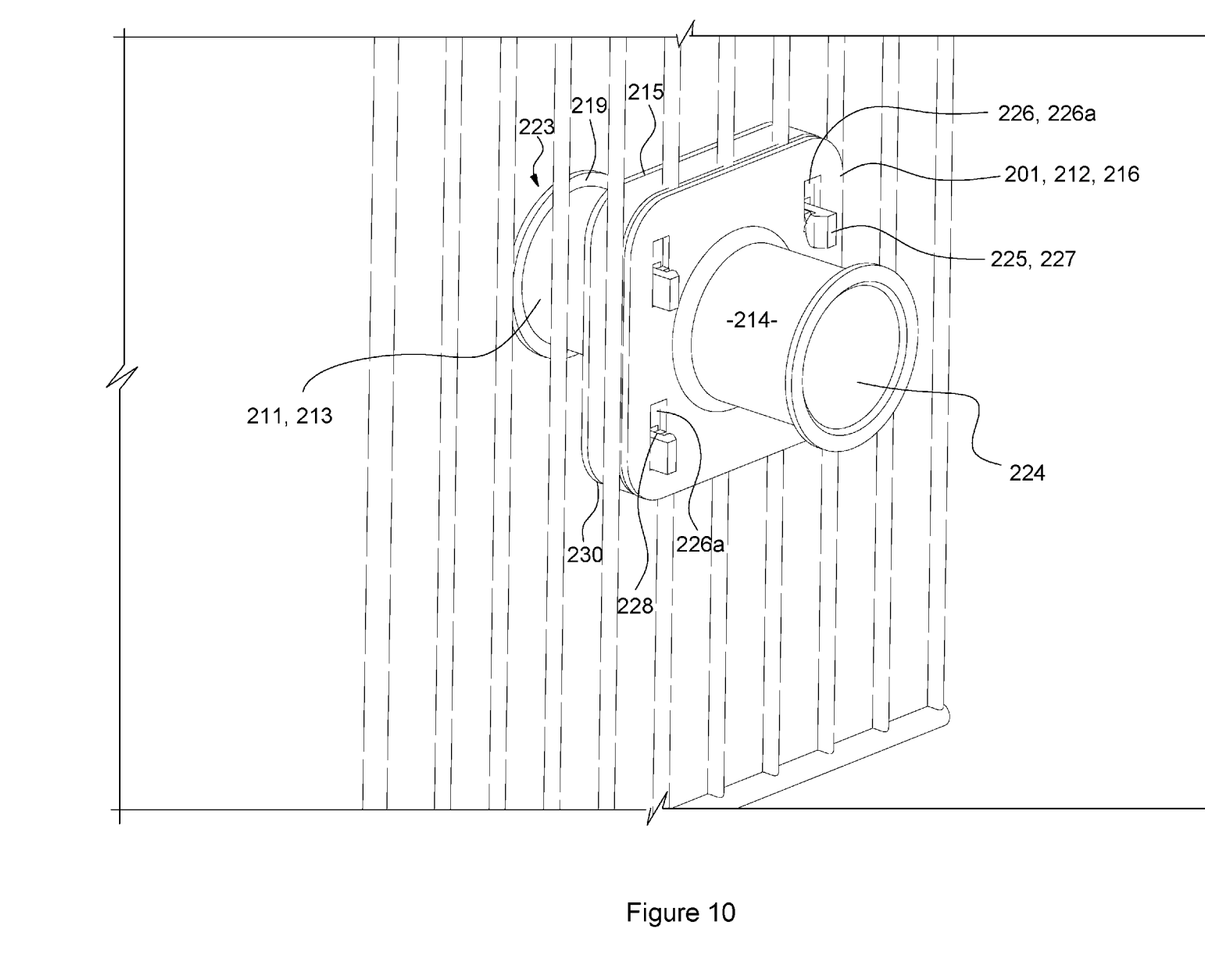
FIG. 10 is a perspective view of the apparatus shown in FIG. 8 with the second duct part slidably moved relative to said first duct part for securing same.

FIGS. 8 to 10 depict a third embodiment of an apparatus device 201, which comprises a first duct part 211 and a second duct part 212, each having respective sleeve portions 213, 214 respectively which define ports 223, 224 of each duct. Each sleeve portion 213, 214 has a square-like shaped flange 215, 216 disposed at one end thereof and integrally formed therewith.

Flange 215 of first duct part 211 has four projections 225, and a sealing member 230 mounted thereto. Each projection 225 has a lower portion 228 and a hooked-head 227 at its free end.

Flange 116 of second duct part 212 has a keyhole-style aperture 226 with the shape of a rectangular portion 226a at one end and an elongate slot 226b of narrower width extending there from. The rectangular portion 226a of keyhole-style aperture 226 is of a size to allow hook-head 227 of projection 25 to pass there through. The dimension of lower portion 228 of projection 225 is slightly smaller in size than the width of elongate slot 226b, so that it can be slid there along.

Apparatus 201 also comprises a sealing arrangement in the form of a sealing member 230 disposed on the side of flange 15 from which headed projections 225 project. Preferably sealing member 230 is a layer of closed cell foam secured to flange 215 by adhesive.

In use, when first duct part 211 and second duct part 212 are to be mounted to cage 3, a user (not shown) brings first duct part 211 towards and against cage door 3, such that headed projections 225 pass through cage 3 and sealing member 230 on flange 215 is abutted and held against the inside of cage 3, such that sealing member 230 compresses around the bars of cage door 3 and portions thereof protrude through cage door 3. With headed projections 225 passed through cage door 3, the user brings second duct part 212 towards them and rectangular portion 226a of each keyhole-style aperture 226 is passed over respective hooked-heads 27 of projections 225. Once, rectangular portions 226a have cleared respective hooked heads 227 and are aligned with respective lower portions 228, second duct part 212 is moved (slid) relative to first duct part 211, thereby having lower portions 28 slide within respective narrow slots 226b. When hook-heads 227 are aligned with respective slots 226b, they cannot be withdrawn from keyhole-style aperture 226, as each hooked-head 227 is larger than its respective slot 226b. During the bringing together and slidable movement of second duct part 212 relative to first duct part 211, sealing member 230 is compressed somewhat. However, once second duct part 212 and first duct part 211 are secured and let go of by the user, the closed cell foam of sealing member 230 will return somewhat towards its pre-compressed state, but as it is "sandwiched" between flanges 215, 216 of respective duct parts 211, 212 sealing member 230 provides an effective seal across the bars of cage door 3 (the barrier).

Each keyhole-style aperture 26 has a rib 29 partially encircling the end of its respective curved slot 26b. This rib 29 acts both as stiffener in the vicinity of slot 26b, but also as an engagement seat for head 27 when projection 25 has been inserted through keyhole-style aperture 26, twisted to slide along slot 26b and locked in place.

Toroidal lip 219 has a similar function to lip 19 of the first embodiment.

It should be understood that whilst the second and third embodiments have different configurations of apparatus 101, 201 attaching first duct parts 111,211 to respective second duct parts 112, 212 the way there respective sleeve portions are connected to conduits or directly to a blanket are similar to that described for the first embodiment.

It should also be understood that whilst the projections 25,125 and 225 in the abovementioned embodiments have spherical-like or rectangular-like heads 27, 127 and 227 to pass through enlarged aperture portions 26a, 126a and 226a of the keyhole-style apertures 26,126 and 226 it should be understood the shape of the heads and enlarged aperture portions may vary from that shown in the embodiments. Likewise it should also be understood that whilst the shape of the flanges 15, 16, 113, 115,116, 2215,216 are in the abovementioned embodiments circular or square in shape, they may in other embodiments of the invention be of different shape.

The terms "comprising" and "including" (and their grammatical variations) as used herein are used in inclusive sense and not in the exclusive sense of "consisting only of".

The invention claimed is:

1. An apparatus for facilitating delivery of conditioned air across a barrier in a cage for holding an animal patient to a blanket arrangement providing the conditioned air to said patient, said apparatus comprising a first duct part, a second duct part and a mounting mechanism, said mounting mechanism arranged to mount said first duct part on one side of said barrier and said second duct part on the other side of said barrier opposite said first duct part, to provide a duct for ducting conditioned air across said barrier irrespective of the arrangement of said barrier, said barrier having a plurality of openings therein, and the apparatus further comprising a seal arrangement to provide at least a partial seal across said barrier, and said mounting mechanism comprises a fastening mechanism for fastening said first and second duct parts to each other across said barrier, wherein said fastening mechanism is a keyhole-style fastening arrangement utilising a plurality of headed projections on a first flange of said first duct part engagable with respective keyhole-style apertures on a second flange of said second duct part, each said keyhole-style aperture has a portion of larger dimension than a slot which extends therefrom, and said seal arrangement comprising a sealing member of closed cell foam having holes therein mounted to said first flange via said plurality of headed projections, and wherein use, said first duct part and said sealing member is positioned from the inside of said barrier with said headed projections passing through said openings in said barrier and said sealing member abutting against said barrier, and with the second duct portion said opposite side of said barrier each said headed portion is inserted into a respective said keyhole-style aperture via said portion of larger dimension, and when said first flange of said first duct part is slidably moved relative to said second flange of said second duct part, each of said headed projections is aligned with a respective said slot of a said keyhole-style aperture, and during engagement of said headed projections of said first duct part with said keyhole-style apertures of said second duct part, said sealing member is compressed, and when said first duct part and said second duct part are secured, said closed cell foam returns towards its pre-compressed state whilst remaining between said first and second duct parts and in engagement with said barrier.

2. An apparatus as claimed in claim 1, wherein each said slot of said keyhole-style aperture is a curved elongate slot which extends there from, and when said first flange of said first duct part is slidably moved relative to said second flange of said second duct part, the relative movement is as a result of a twist action.

3. An apparatus as claimed in claim 2, wherein each said keyhole aperture has a rib disposed at or near the periphery of the closed end of said elongate slot.

4. An apparatus as claimed in claim 1, wherein each said slot of said keyhole-style aperture is a straight elongate slot which extends there from, and when said headed projections are inserted into said keyhole-style aperture they are inserted through said portion of larger dimension, and when said first flange of said first duct part is slidably moved relative to said second flange of said second duct part, the relative movement is of a linear action.

5. An apparatus for facilitating delivery of conditioned air across a barrier in a cage for holding an animal patient to a blanket arrangement providing the conditioned air to said patient, said barrier having a plurality of openings therein, said apparatus comprising:
- a first duct part having a first flange including a plurality of headed projections;
- a second duct part having a second flange including a plurality of keyhole-style apertures, each said keyhole-style aperture has a portion of larger dimension than a curved elongate slot which extends there from;
- a toroidal sealing member of closed cell foam having holes therein mounted to said first flange via said plurality of headed projections; and
- wherein in use said first duct part and said seal is positioned from the inside of said barrier with said headed projections passing through said barrier and said toroidal sealing member abutting against said barrier, and with said second duct part on said opposite side of said cage each said headed projection is inserted into a respective said keyhole-style aperture via said portion of larger dimension, and when said first flange of said first duct is slidably moved relative to said second flange of said first second part, the relative movement is as a result of a twist action, and each said headed projections is aligned with a respective said curved elongate slot of a said keyhole-style aperture, and during the engagement of said headed projections of said first duct part with said respective keyhole-style apertures of said second duct part, said toroidal sealing member is compressed, and when said first duct part and second duct part are secured, said closed cell foam returns towards its pre-compressed state whilst remaining between said first and second duct parts and in engagement with said barrier.

* * * * *